United States Patent
Bannae et al.

(10) Patent No.: US 9,962,106 B2
(45) Date of Patent: May 8, 2018

(54) MEDICAL IMAGE PROCESSING APPARATUS AND MEDICAL IMAGE PROCESSING METHOD

(71) Applicant: TOSHIBA MEDICAL SYSTEMS CORPORATION, Otawara-Shi (JP)

(72) Inventors: Shuhei Bannae, Otawara (JP); Shigeharu Ohyu, Yaita (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 103 days.

(21) Appl. No.: 15/013,802

(22) Filed: Feb. 2, 2016

(65) Prior Publication Data
US 2016/0239958 A1    Aug. 18, 2016

(30) Foreign Application Priority Data
Feb. 13, 2015   (JP) ................. 2015-026131

(51) Int. Cl.
  *G06T 7/00*   (2017.01)
  *A61B 5/055*   (2006.01)
  (Continued)

(52) U.S. Cl.
  CPC ............ *A61B 5/055* (2013.01); *A61B 5/0263* (2013.01); *A61B 5/489* (2013.01); *G06T 7/0016* (2013.01);
  (Continued)

(58) Field of Classification Search
  CPC ..... G06T 11/003; G06T 7/0016; G06T 7/215; G06T 2207/10088; G06T 2207/30101;
  (Continued)

(56) References Cited

U.S. PATENT DOCUMENTS 6,654,628 B1 * 11/2003 Silber .................... A61B 5/055
                                                             600/410

FOREIGN PATENT DOCUMENTS

JP    2002-501774    1/2002
JP    2007-135894    6/2007
(Continued)

OTHER PUBLICATIONS

Oyre et al. "In vivo Wall Shear Stress Measured by Magnetic Resonance Velocity Mapping in the Normal Human Abdominal Aorta." European Journal of Vascular and Endovascular Surgery, vol. 13, issue 3, Mar. 1997, pp. 263-271.*

(Continued)

*Primary Examiner* — Jon Chang
(74) *Attorney, Agent, or Firm* — Oblon, McClelland, Maier & Neustadt, L.L.P.

(57) ABSTRACT

A medical image processing apparatus according to one of present embodiments includes processing circuitry. The processing circuitry is configured to calculate fluid information including a velocity vector based on three-dimensional phase image data in multiple time phases, the three-dimensional phase image data being collected by phase contrast magnetic resonance imaging, and the three-dimensional phase image data representing a fluid flowing through a lumen. The processing circuitry is configured to identify a wall region of the lumen based on the velocity vector. The processing circuitry is configured to calculate wall shear stress using the wall region and the fluid information.

13 Claims, 9 Drawing Sheets

(51) Int. Cl.
- *A61B 5/026* (2006.01)
- *G06T 11/00* (2006.01)
- *A61B 5/00* (2006.01)
- *G06T 7/215* (2017.01)
- *A61B 5/02* (2006.01)

(52) U.S. Cl.
CPC ............ G06T 7/215 (2017.01); G06T 11/003 (2013.01); *A61B 5/02007* (2013.01); *G06T 2207/10076* (2013.01); *G06T 2207/10088* (2013.01); *G06T 2207/30101* (2013.01); *G06T 2207/30104* (2013.01)

(58) Field of Classification Search
CPC . G06T 2207/10076; G06T 2207/30104; A61B 5/055; A61B 5/0263; A61B 5/489; A61B 5/026; A61B 5/02007

See application file for complete search history.

(56) References Cited

FOREIGN PATENT DOCUMENTS

| | | |
|---|---|---|
| JP | 2013-534154 | 9/2013 |
| WO | WO 99/38433 A1 | 8/1999 |
| WO | WO 2012/021307 A2 | 2/2012 |

OTHER PUBLICATIONS

Potters et al. "Measuring Wall Shear Stress Using Velocity-Encoded MRI." Current Cardiovascular Imaging Reports, 7:9257, Apr. 2014, 12 pages.*

Sui et al. "Assessment of Wall Shear Stress in the Common Carotid Artery of Healthy Subjects Using 3.0-Tesla Magnetic Resonance." Acta Radiologica, 49:4, pp. 442-449.*

Papathanasopoulou et al. "MRI Measurement of Time-Resolved Wall Shear Stress Vectors in a Carotid Bifurcation Model, and Comparison with CFD Predictions." Journal of Magnetic Resonance Imaging, 17, 2003, pp. 153-162.*

Wu et al. "Three-dimensional Phase Contrast Velocity Mapping Acquisition Improves Wall Shear Stress Estimation in vivo." Magnetic Resonance Imaging, 22, 2004, pp. 345-351.*

Stalder et al. "Quantitative 2D and 3D Phase Contrast MRI: Optimized Analysis of Blood Flow and Vessel Wall Parameters." Magnetic Resonance in Medicine, 60, 2008, pp. 1218-1231.*

* cited by examiner

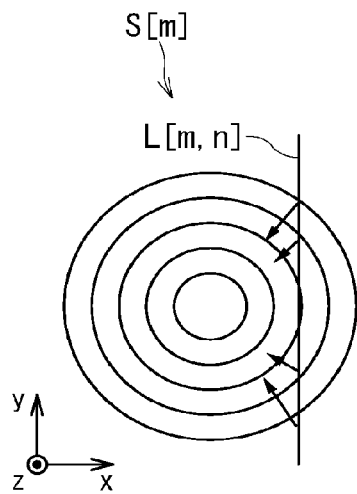 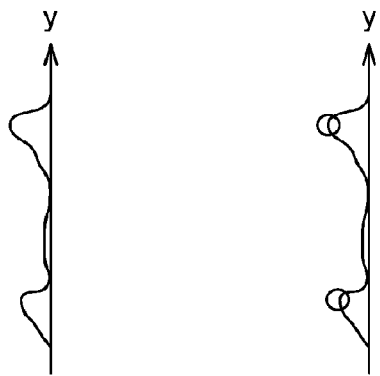
FIG. 6A    FIG. 6B    FIG. 6C
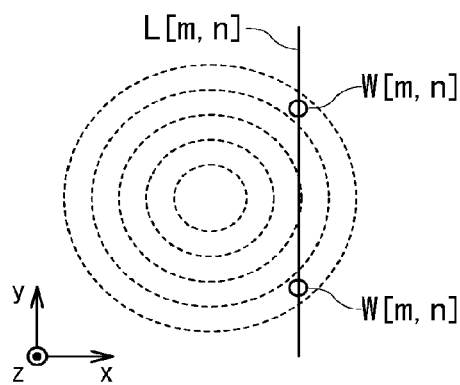 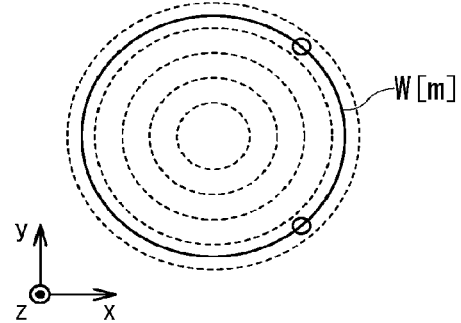
FIG. 6D    FIG. 6E

MEDICAL IMAGE PROCESSING APPARATUS AND MEDICAL IMAGE PROCESSING METHOD

CROSS-REFERENCE TO RELATED APPLICATION

This application is based upon and claims the benefit of priority from Japanese Patent Application No. 2015-26131, filed on Feb. 13, 2015, the entire contents of which are incorporated herein by reference.

FIELD

Embodiments described herein relate generally to a medical image processing apparatus and a medical image processing method.

BACKGROUND

A magnetic resonance imaging (MRI) apparatus is an imaging apparatus which excites nuclear spins in a patient placed in a static magnetic field with a radio frequency (RF) signal of Larmor frequency and thereby generates an image by reconstructing a magnetic resonance signal generated from the patient as a result of the excitation. Unlike medical image generating apparatus which uses X-rays, the MRI apparatus does not cause radiation exposure, and thus has spread in medical scenes as an apparatus capable of low-invasive diagnostic imaging.

In the field of MRI, a technique is available which can obtain information about a four-dimensional three-directional velocity vector made up of three spatial dimensions and multiple time phases. This field is generally known as 4D Flow. 4D Flow uses a technique which is called a phase contrast method and is capable of measuring flow velocity as a phase, and blood flow information can be obtained non-invasively from data provided by 4D Flow.

Flow velocity, flow rate, and, wall shear stress (WSS) can be found from the data provided by 4D Flow. A conventional technique obtains vascular information from intensity images provided by 4D Flow and images obtained by a separate scan and uses vascular information for WSS calculation.

WSS heavily depends on vascular information, i.e., extraction accuracy of a vascular wall region. However, in the conventional technique, four-dimensional image data which is provided by 4D Flow and can be used to calculate four-dimensional velocity vector data has a low spatial resolution, making it difficult to find a correct vascular wall region from the image data.

Also, changes in the vascular wall region caused by cardiac cycles cannot be drawn from high-resolution image data obtained by scanning separately from 4D Flow according the conventional technique, which results in reduced calculation accuracy of WSS.

One of problems to be solved by the present invention is to provide a medical image processing apparatus and a medical image processing method which can improve calculation accuracy of WSS.

BRIEF DESCRIPTION OF THE DRAWINGS

In accompanying drawings,

FIGS. 6A to 6E are diagrams to illustrate a concept of calculating a vascular wall region;

DETAILED DESCRIPTION

A medical image processing apparatus and a medical image processing method according to the present embodiments will be described with reference to the accompanying drawings.

The medical image processing apparatus according to one of the present embodiments includes processing circuitry. The processing circuitry is configured to calculate fluid information including a velocity vector based on three-dimensional phase image data in multiple time phases, the three-dimensional phase image data being collected by phase contrast magnetic resonance imaging, and the three-dimensional phase image data representing a fluid flowing through a lumen. The processing circuitry is configured to identify a wall region of the lumen based on the velocity vector. The processing circuitry is configured to calculate wall shear stress using the wall region and the fluid information.

First Embodiment

Figure 1:
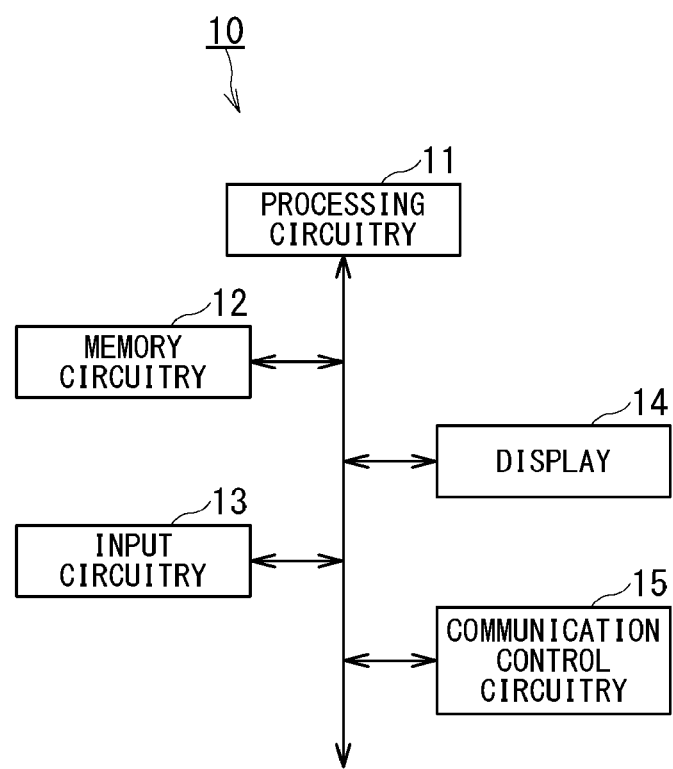
FIG. 1 is a schematic diagram showing a hardware configuration of a medical image processing apparatus according to a first embodiment.

FIG. 1 is a schematic diagram showing a hardware configuration of a medical image processing apparatus according to a first embodiment.

FIG. 1 shows the medical image processing apparatus 10 according to the first embodiment. Note that the medical image processing apparatus 10 may be provided on a medical imaging system connected with various apparatus such as a medical image generating apparatus (medical diagnostic imaging apparatus), medical image management apparatus (image server), and image interpretation terminal (none is shown) via a network. The medical image generating apparatus is designed to generate medical image data. The medical image management apparatus is designed to store and manage medical image data. The image interpretation terminal is designed to receive medical image data from the medical image management apparatus and display the medical image data on a display in order for a physician to interpret the medical image data.

Although description will be given of an example in which the medical image processing apparatus 10 alone implements functions described below, these functions may be distributed to components of a medical imaging system so as to be implemented by the medical imaging system as a whole.

The medical image processing apparatus 10 includes processing circuitry 11, memory circuitry 12, input circuitry 13, a display 14, and communication control circuitry 15.

The processing circuitry 11 includes a CPU (central processing unit), and a RAM (random access memory). The processing circuitry 11 reads various control programs stored in the memory circuitry 12, performs various calculations, and exerts overall control over processing operations of the various circuits 12 to 15.

The memory circuitry 12 includes a memory, and an HDD (hard disc drive). The memory circuitry 12 stores data needed for execution of control programs used by the processing circuitry 11, data received from a medical image generating apparatus such as an MRI apparatus, a medical image management apparatus (neither is shown), and the like via a communication control circuitry 15 or removable media, and data generated by the processing circuitry 11.

The input circuitry 13 includes a keyboard, and a mouse. When operated by an operator, the input circuitry 13 generates an operation signal corresponding to the operation and outputs the signal to the processing circuitry 11. The input circuitry 13 may include a touch panel constructed integrally with the display 14.

The display 14 is a display unit such as an LCD (liquid crystal display). On instructions from the processing circuitry 11, the display 14 displays various operation screens as well as various display information including data generated by the processing circuitry 11.

The communication control circuitry 15 includes connectors compliant with parallel connection specifications or serial connection specifications. The medical image processing apparatus 10 exchanges information with external apparatus on a network via the communication control circuitry 15. For example, the medical image processing apparatus 10 performs communications with respect to external apparatus via the communication control circuitry 15, as follows: receives data from the medical image generating apparatus, medical image management apparatus (neither is shown), or the like and transmits data generated by the processing circuitry 11 to the medical image management apparatus or image interpretation terminal (neither is shown).

Figure 2:
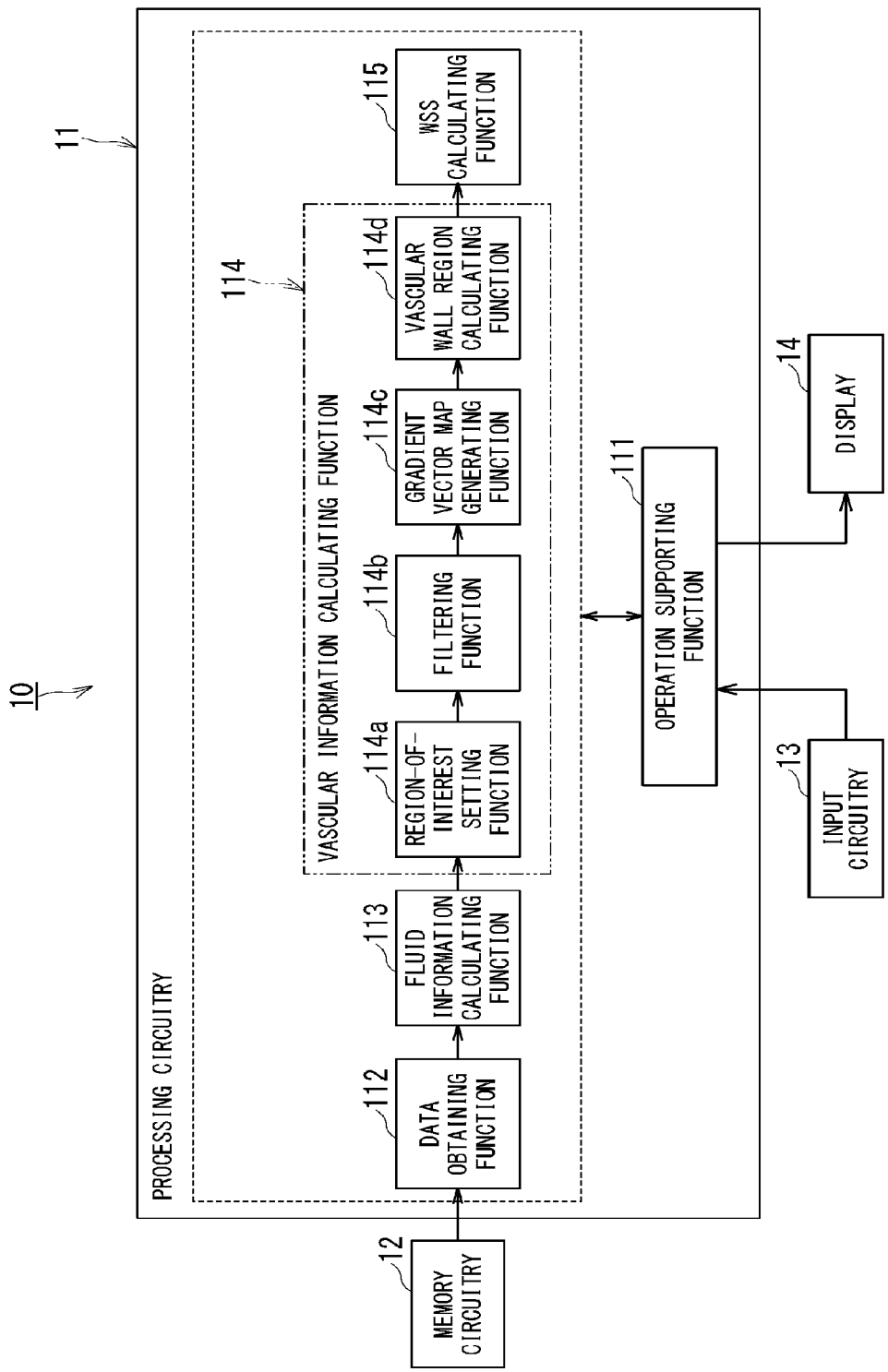
FIG. 2 is a block diagram showing functions of the medical image processing apparatus according to the first embodiment.

FIG. 2 is a block diagram showing functions of the medical image processing apparatus 10 according to the first embodiment.

As the processing circuitry 11 executes programs, the medical image processing apparatus 10 implements an operation supporting function 111, a data obtaining (reading) function 112, a fluid information calculating function 113, a vascular information calculating function 114, and a WSS calculating function 115.

Note that although it is assumed in the example described below that the functions 111 to 115 of the medical image processing apparatus 10 operate in software fashion, some or all of the functions 111 to 115 may be provided in the medical image processing apparatus 10 in hardware fashion.

The operation supporting function 111 is a user interface such as a graphical user interface (GUI) which uses a lot of graphics in displaying information for the operator on the display 14, allowing the operator to perform most of basic operations via the input circuitry 13.

The data obtaining function 112 obtains (reads) four-dimensional image data (four-dimensional blood flow image data), which is three-dimensional image data in multiple time phases, the three-dimensional image data being stored in the memory circuitry 12 and used to calculate a four-dimensional velocity vector made up of three spatial dimensions and the multiple time phases. The four-dimensional image data undergoes a data conversion process, as required, to enable a blood flow analysis process. For example, image data in DICOM (digital imaging and communications in medicine) format is used as four-dimensional image data.

For example, the four-dimensional image data is generated based on four-dimensional phase image data, which is three-dimensional phase image data in multiple time phases, the three-dimensional phase image data being obtained by phase contrast magnetic resonance imaging. The phase contrast magnetic resonance imaging is called 4D-Flow or 3D phase contrast cine magnetic resonance imaging (3D PC cine MRI). The phase contrast magnetic resonance imaging is an imaging method capable of collecting four-dimensional image data in which each voxel contains blood flow vector information made up of three velocity components.

Specifically, the phase contrast magnetic resonance imaging performs velocity encoding by applying a bipolar gradient magnetic field in each of an x-axis, y-axis, z-axis and obtains one item of three-dimensional flow velocity image data on each axis from two phases of three-dimensional phase image data. Then, one item of three-dimensional image data in which each voxel contains blood flow vector information made up of three velocity components is calculated from the three-dimensional flow velocity image data on the three axes. The three-dimensional image data in multiple time phases is referred to as four-dimensional image data.

The four-dimensional image data may be not only four-dimensional image data based on four-dimensional phase image data from the MRI apparatus, but also any image data which is obtained using a medical diagnostic imaging apparatus such as X-ray CT (computed tomography) apparatus or a rotational angiography apparatus and which allows four-dimensional velocity vector data to be calculated.

The fluid information calculating function 113 calculates fluid information (flow velocity, flow rate, and the like) including four-dimensional blood flow velocity vector data (four-dimensional three-component blood flow velocity information), which is three-dimensional blood flow velocity vector data in multiple time phases, based on the four-dimensional image data obtained by the data obtaining function 112. Each voxel of the four-dimensional blood flow velocity vector data contains blood flow information made up of three successive velocity components.

The vascular information calculating function 114 sets a region of interest based on the four-dimensional blood flow velocity vector data calculated by the fluid information calculating function 113 and calculates vascular information including information on a vascular wall region, based on the four-dimensional blood flow velocity vector data on the region of interest. The vascular information calculating function 114 can calculate vascular information in multiple time phases, i.e., four-dimensional vascular information, as well as calculate a single piece of vascular information (three-dimensional vascular information) by integrating vascular information in multiple time phases (through integration or arithmetic averaging). The vascular information calculating function 114 includes a region-of-interest setting function 114a, a filtering function 114b, a gradient vector map generating function 114c, and a vascular wall region calculating function 114d.

The region-of-interest setting function 114a marks out a region (region of interest) with any flow in the four-dimensional blood flow velocity vector data calculated by the fluid information calculating function 113. The region-of-interest setting function 114a establishes a set of voxels whose blood flow velocity vector is equal to or larger in magnitude (vector length) than a threshold as a region of interest by selecting them from among the voxels in the four-dimensional blood flow velocity vector data.

The region-of-interest setting function 114a sets one region of interest based on data in a certain time phase out of the four-dimensional blood flow velocity vector data and applies the one region of interest to data at corresponding position in another time phase in the four-dimensional blood flow velocity vector data. Alternatively, the region-of-interest setting function 114a sets one region of interest based on data obtained by integrating data in multiple time phases (through integration or arithmetic averaging) out of the four-dimensional blood flow velocity vector data and applies the one region of interest to the data at corresponding positions in the multiple time phases. The latter approach can more clearly distinguish between a still region and a region with a flow present therein, improving accuracy of detecting the region in which a flow is present.

The region of interest may be set manually. On a display image showing the four-dimensional blood flow velocity vector data calculated by the fluid information calculating function 113, the region-of-interest setting function 114a may manually set a region of interest according to a command entered from the input circuitry 13 operated by the operator via the operation supporting function 111.

Figure 3:
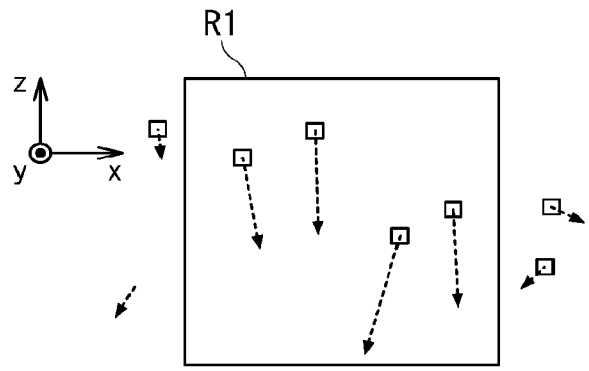
FIG. 3 is a diagram to illustrate a concept of setting a region of interest.

FIG. 3 is a diagram to illustrate a concept of setting a region of interest.

Figure 7:
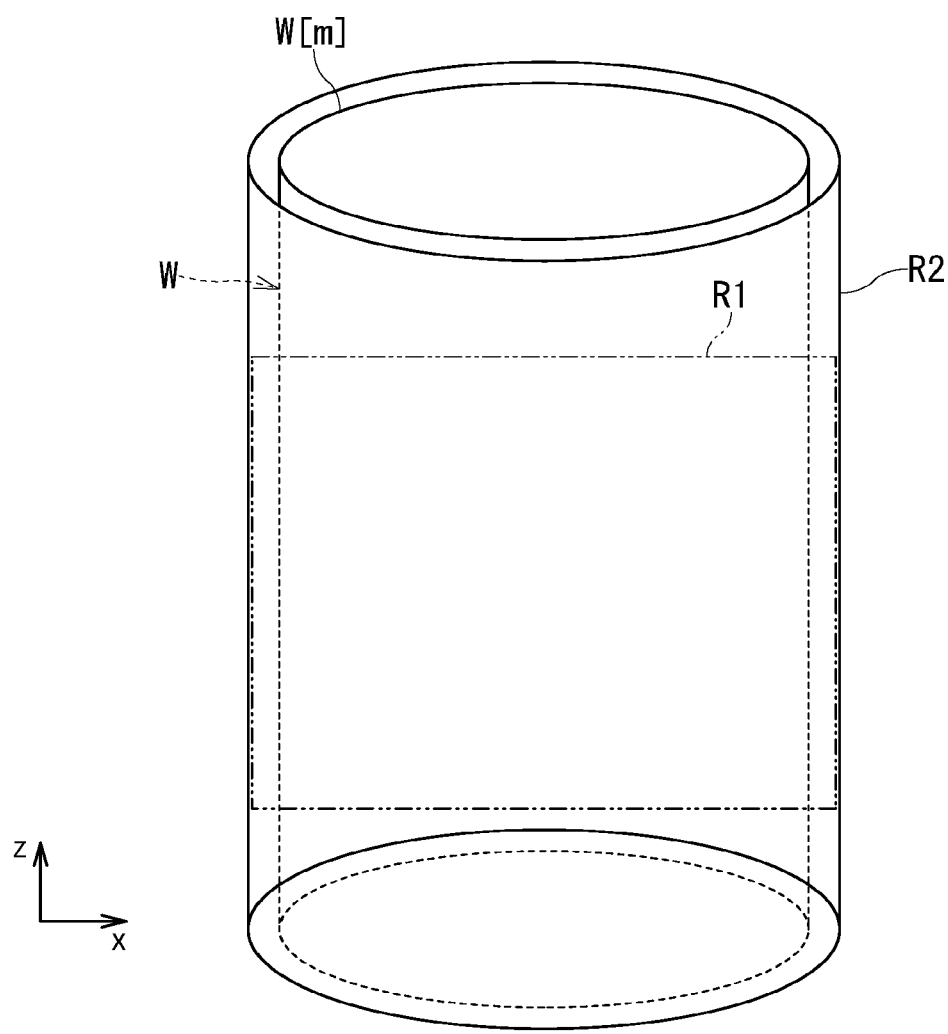
FIG. 7 is a diagram to illustrate a concept of a vascular wall region over multiple slices.

As shown in FIG. 3, on four-dimensional blood flow velocity vector data (data in a certain time phase or integrated data), a set of voxels having a blood flow velocity vector equal to or larger in magnitude than the threshold is established as a two-dimensional region of interest R1. Note that the region of interest R1 is also illustrated in FIG. 7.

Referring back to FIG. 2, based on data, in each time phase, of the four-dimensional blood flow velocity vector data calculated by the fluid information calculating function 113, the filtering function 114b performs a smoothing process on a blood flow velocity vector on each slice in the region of interest using a low pass filter, the region of interest having been set by the region-of-interest setting function 114a. Consequently, the four-dimensional blood flow velocity vector data is smoothed with any low frequency component (noise component) being removed from each slice of the region of interest R1.

Figure 4:
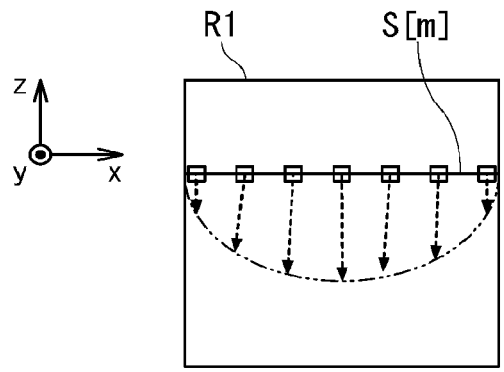
FIG. 4 is a diagram to illustrate a concept of a smoothing process.

FIG. 4 is a diagram to illustrate a concept of a smoothing process.

As shown in FIG. 4, based on each item of the three-dimensional blood flow velocity vector data in four-dimensional blood flow velocity vector data, the blood flow velocity vector on a m-th (m=1, 2, . . . , M) slice (slice S[m]) in the region of interest R1 is subjected to a smoothing process by a low pass filter. In the example of FIG. 4, the slice S[m] is cut along an x-y plane, but this is not restrictive.

Referring back to FIG. 2, on the slice S[m] in the region of interest, the gradient vector map generating function 114c determines an absolute value V[m] (Vx, Vy, Vz) of blood flow velocity for each voxel subjected to a smoothing process by the filtering function 114b. Using the following expression, the gradient vector map generating function 114c determines a gradient vector ∇V[m] (grad V[m]) which represents a direction in which a magnitude of the velocity absolute value V[m] changes most sharply. That is, the gradient vector map generating function 114c determines a direction on the vascular slice S[m], i.e., a gradient vector on a minor axis section of the blood vessel.

$$\nabla V[m] = \left( \frac{\delta V[m]}{\delta x}, \frac{\delta V[m]}{\delta y}, \frac{\delta V[m]}{\delta z} \right)$$

The gradient vector map generating function 114c generates, based on gradient vectors of the slice S[m] in the region of interest, a gradient vector map of the slice S[m].

Figure 5:
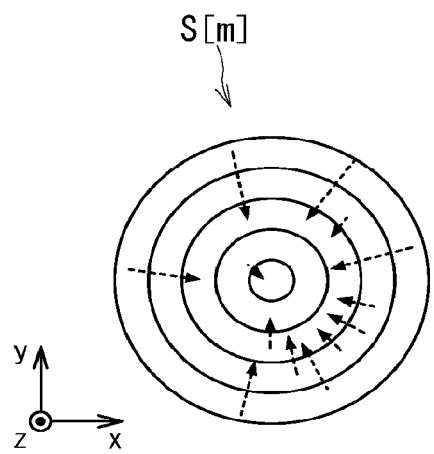
FIG. 5 is a diagram showing an example of a gradient vector map.

FIG. 5 is a diagram showing an example of a gradient vector map.

FIG. 5 is a diagram showing a gradient vector map of a slice S[m] with directions of gradient vectors placed at voxel locations on the slice S[m]. On the gradient vector map of the slice S[m] shown in FIG. 5, the gradient vectors on an outer side (on the side of a vascular wall) have relatively large magnitudes, with the gradient vectors decreasing in magnitude toward a center.

Referring back to FIG. 2, based on the gradient vector map generated by the gradient vector map generating function 114c the vascular wall region calculating function 114d detects a region in which the magnitude of the gradient vector is equal to or larger than a threshold and calculates the region as a vascular wall region for use to determine WSS. The vascular wall region calculating function 114d may display the vascular wall region on the display 14 via the operation supporting function 111. In that case, the vascular wall region may be displayed by being distinguished from a fluid portion.

FIGS. 6A to 6E are diagrams to illustrate a concept of calculating a vascular wall region.

As shown in FIG. 6A, an n-th (n=1, 2, . . . , N) straight line L[m, n] is assigned to the gradient vector map of the slice S[m] in one direction (y direction in FIG. 6A) and a distribution (FIG. 6B) is generated with magnitudes of voxels' gradient vectors plotted on the voxels on the straight line L[m, n].

Next, two local maximum points of the distribution shown in FIG. 6B are determined (FIG. 6C). Locations of the two local maximum points shown in FIG. 6C are set as a vascular wall region W[m, n] on the straight line L[m, n] (FIG. 6D).

Furthermore, locations of two local maximum values on each of straight lines L[m, 1] to L[m, N] on the slice S[m] are determined, vascular wall regions W[m, 1] to W[m, N] on the straight lines L[m, 1] to L[m, N] are established, and thereby a vascular wall region W[m] is established (FIG. 6E).

Referring back to FIG. 2, by calculating vascular wall regions W[1] to W[M] in slices S[1] to S[M], respectively, the vascular information calculating function 114 can calculate a three-dimensional vascular wall region W across the slices. By repeating a process of calculating the three-dimensional vascular wall region W in four-dimensional blood flow velocity vector data in all time phases, the vascular information calculating function 114 can calculate a four-dimensional vascular wall region W.

FIG. 7 is a diagram to illustrate a concept of a vascular wall region W over multiple slices.

FIG. 7 shows a vascular wall region W[m] in a slice S[m] in a three-dimensional region of interest R2. By calculating the vascular wall regions W [1] to W[M] in the slices S[1] to S[M], respectively, in the region of interest R2, the vascular wall region W over the slices S[1] to S[M] is calculated in the region of interest R2.

Referring back to FIG. 2, the WSS calculating function 115 calculates WSS based on the fluid information calculated by the fluid information calculating function 113 and the vascular information including the four-dimensional vascular wall region W calculated by the vascular information calculating function 114. The WSS calculating function 115 displays WSS of the vascular wall region W on the display 14 via the operation supporting function 111.

Specifically, based on the four-dimensional blood flow velocity vector data on the region of interest, the WSS calculating function 115 calculates a wall shear rate "dv/ds" of the vascular wall region W (illustrated in FIG. 7) in the region of interest R2 (illustrated in FIG. 7), where "dv" is flow velocity of blood flow along the vascular wall region W and "ds" is a distances from the vascular wall region W to a measurement site of the flow velocity dv. Next, the WSS calculating function 115 multiplies the wall shear rate by viscosity and thereby calculates WSS of the vascular wall region W.

Figure 8:
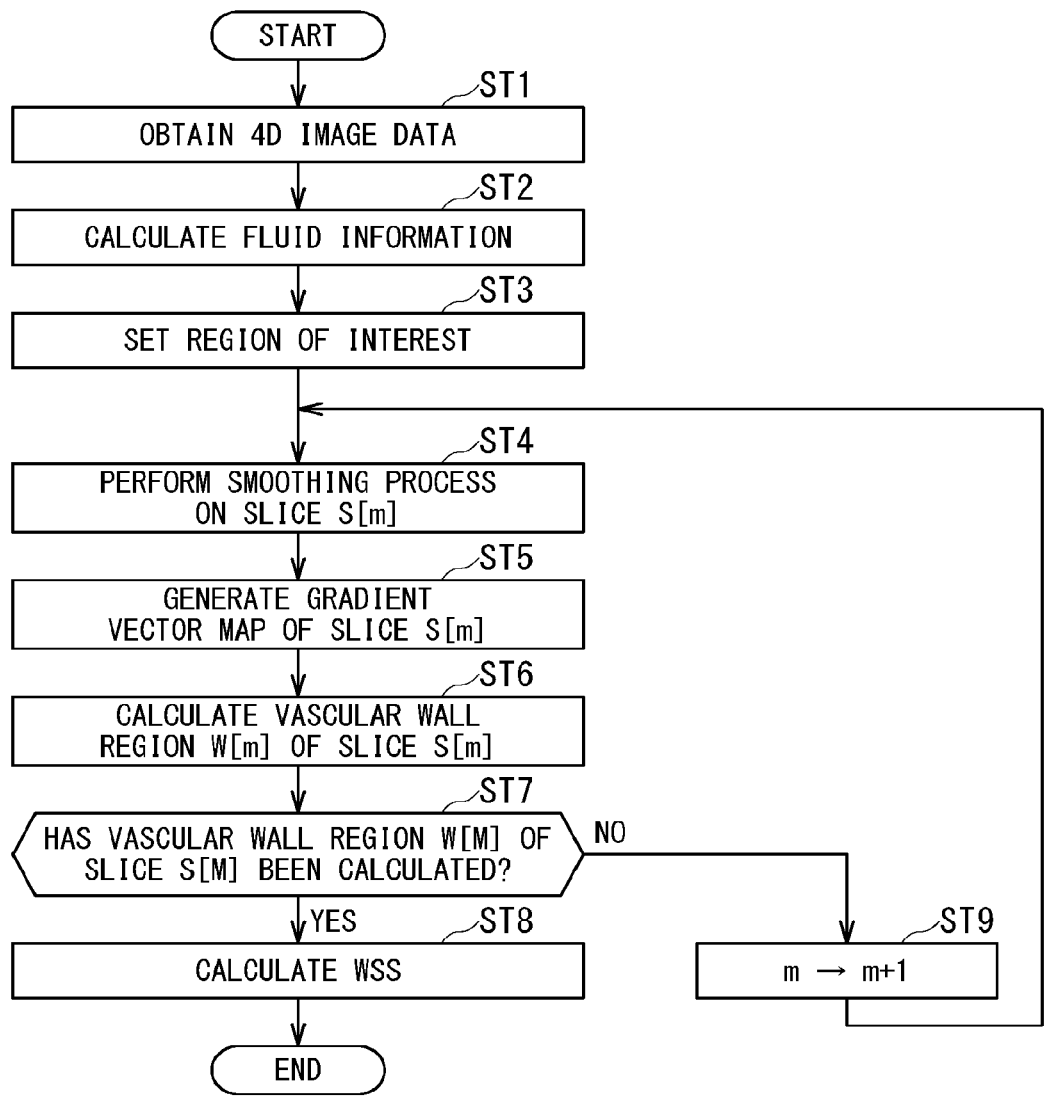
FIG. 8 is a flowchart showing an operation of the medical image processing apparatus according to the first embodiment.

FIG. 8 is a flowchart showing an operation of the medical image processing apparatus 10 according to the first embodiment.

The medical image processing apparatus 10 obtains four-dimensional image data stored in the memory circuitry 12 and used to calculate a four-dimensional velocity vector made up of three spatial dimensions and multiple time phases (step ST1). Based on four-dimensional image data obtained in step ST1, the medical image processing apparatus 10 calculates fluid information including four-dimensional blood flow velocity vector data (four-dimensional three-component blood flow velocity information), which is three-dimensional blood flow velocity vector data in the multiple time phases (step ST2).

The medical image processing apparatus 10 sets a region of interest based on the four-dimensional blood flow velocity vector data calculated in step ST2 (step ST3). A method used in step ST3 to set a region of interest is as described with reference to FIG. 3.

Based on data in a certain time phase out of the four-dimensional blood flow velocity vector data calculated in step ST2, the medical image processing apparatus 10 performs a smoothing process on the blood flow velocity vector on the m-th slice S[m] in the region of interest established in step ST3, using a low pass filter, and thereby smoothes the m-th slice S[m] with any low frequency component being removed therefrom (step ST4). A smoothing method used in step ST4 is as described with reference to FIG. 4.

On the slice S[m] in the region of interest, the medical image processing apparatus 10 determines the absolute value V[m] (Vx, Vy, Vz) of blood flow velocity for each voxel subjected to the smoothing process in step ST4, and thereby determines a gradient vector which represents the direction in which the magnitude of the velocity absolute value V[m] changes most sharply. Then, based on the gradient vectors of the voxels contained in the slice S[m], the medical image processing apparatus 10 generates a gradient vector map of the slice S[m] (step ST5). An example of the gradient vector map is shown in FIG. 5.

Based on the gradient vector map of the slice S[m] generated in step ST5, the medical image processing apparatus 10 detects a region in which the magnitude of the gradient vector is equal to or larger than a threshold and calculates the region as a vascular wall region W[m] for use to determine WSS (step ST6).

The medical image processing apparatus 10 determines whether the M-th vascular wall region W[M] in the region of interest established in step ST3 has been calculated (step ST7). When the determination in step ST7 is YES, i.e., when it is determined that the M-th vascular wall region W[M] in the region of interest has been calculated, the medical image processing apparatus 10 calculates WSS based on the fluid information calculated in step ST2 and the vascular wall region W (illustrated in FIG. 7) made up of the vascular wall regions W[1] to W[M] (step ST8).

On the other hand, the determination in step ST7 is NO, i.e., when it is determined that the M-th vascular wall region W[M] in the region of interest has not been calculated, the medical image processing apparatus 10 increments the slice number from m to m+1 (step ST9) and performs a smoothing process on the (m+1)-th slice S[m+1] (step ST4).

By repeating the processes of steps ST4 to ST9 based on the four-dimensional blood flow velocity vector data in all the time phases using the region of interest established in step ST3, the medical image processing apparatus 10 can calculate the four-dimensional vascular wall region W.

The medical image processing apparatus 10 according to the first embodiment can accurately and precisely calculate the vascular wall region used to calculate WSS, based on the four-dimensional image data which can be used to calculate a four-dimensional velocity vector made up of three spatial dimensions and multiple time phases.

Second Embodiment

Figure 9:
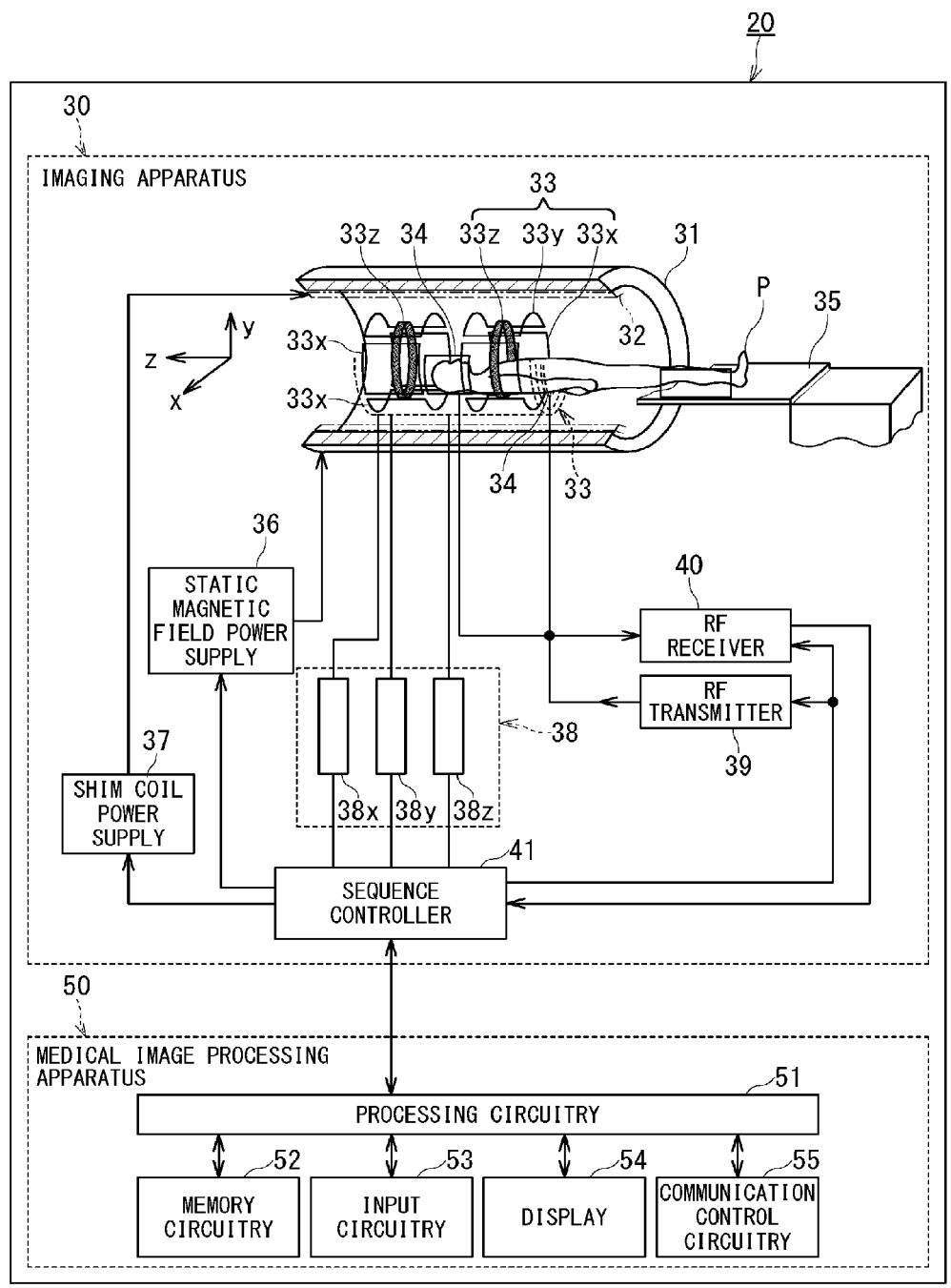
FIG. 9 is a schematic diagram showing a hardware configuration of an MRI apparatus according to a second embodiment.

FIG. 9 is a schematic diagram showing a hardware configuration of an MRI apparatus according to a second embodiment.

FIG. 9 shows the MRI apparatus 20 according to the second embodiment. The MRI apparatus 20 includes an imaging apparatus 30 and a medical image processing apparatus 50.

The imaging apparatus 30 includes a static magnetic field generator (static field magnet) 31, a shim coil 32, a gradient magnetic field generator 33, an RF coil 34, a bed 35, a static magnetic field power supply 36, a shim coil power supply 37, a gradient magnetic field power supply 38, an RF transmitter 39, an RF receiver 40, and a sequence controller 41.

Here, as an example, x, y, and z directions of a device coordinate system which are orthogonal to one another are defined as follows. First, it is assumed that axial directions of the static magnetic field generator 31 and shim coil 32 correspond to the z direction, being arranged to be orthogonal to a vertical direction. It is assumed that the y direction corresponds to the vertical direction and that the bed 35 is placed such that a normal direction of a mounting surface on a table of the bed 35 will correspond to the y direction. Note that the x, y, and z directions according to the second embodiment do not necessarily coincide with the x, y, and z directions according to the first embodiment.

The static magnetic field generator 31 is connected with the static magnetic field power supply 36 and forms a static magnetic field in an imaging space using an electric current supplied from the static magnetic field power supply 36. The static magnetic field generator 31 is often made of a superconducting coil and is connected with the static magnetic field power supply 36 during excitation to draw electric current, but generally becomes disconnected once excited. Note that the static magnetic field generator 31 may be made of a permanent magnet without installing the static magnetic field power supply 36.

The shim coil 32 is connected to the shim coil power supply 37, and makes the static magnetic field uniform using electric current supplied from the shim coil power supply 37.

The gradient magnetic field generator 33 is provided with an x-axis gradient coil 33x, a y-axis gradient coil 33y, and a z-axis gradient coil 33z and formed inside the static magnetic field generator 31. The x-axis gradient coil 33x, y-axis gradient coil 33y, and z-axis gradient coil 33z are connected to the x-axis gradient power supply 38x, y-axis gradient power supply 38y, and z-axis gradient power supply 38z, respectively. The gradient coils 33x, 33y, and 33z form an x-axis gradient magnetic field Gx, y-axis gradient magnetic field Gy, and z-axis gradient magnetic field Gz, respectively, in the imaging space.

That is, if the gradient magnetic fields Gx, Gy, and Gz in three directions of the device coordinate system are combined, a slice selection direction for a gradient magnetic field Gss, a phase encoding direction for a gradient magnetic field Gpe, and a readout direction (frequency encoding direction) for a gradient magnetic field Gro can be established as logical axes, as desired. The gradient magnetic fields in the slice selection direction, phase encoding direction, and readout direction are superposed on the static magnetic field.

The RF coil 34 includes a transmitter coil and a receiver coil. The transmitter coil receives an RF pulse from the RF transmitter 39 and transmits the RF pulse to a subject P. The receiver coil receives an MR signal (high frequency signal) generated when atomic nuclear spins in the subject P are excited with an RF pulse, and the MR signal is detected by the RF receiver 40.

The bed 35 is structured to be able to put the subject P thereon.

The RF transmitter 39 generates an RF pulse (RF current pulse) of Larmor frequency needed to produce nuclear magnetic resonance based on control information received from the sequence controller 41 and transmits the RF pulse to a transmitting RF coil 34. RF coils 34 include a whole body coil incorporated in a gantry and used to transmit and receive RF pulses, and a local coil installed near the bed 35 or subject P and used to receive RF pulses.

The RF receiver 40 performs various signal processing including preliminary amplification, intermediate frequency conversion, phase detection, low frequency amplification, and filtering on the detected MR signal, then performs A/D (analog to digital) conversion, and thereby generates raw data which is digitized complex data. The RF receiver 40 inputs the generated raw data of the MR signal to the sequence controller 41.

On instructions from the medical image processing apparatus 50, the sequence controller 41 stores control information needed to drive the gradient magnetic field power supply 38, RF transmitter 39, and RF receiver 40. The control information as referred to herein means, for example, sequence information describing operational control information such as intensity, application duration, and application timing of a pulsed current to be applied to the gradient power supply 38.

The sequence controller 41 drives the gradient power supply 38, RF transmitter 39, and RF receiver 40 according to a stored predetermined sequence and thereby generates x-axis gradient magnetic field Gx, y-axis gradient magnetic field Gy, and z-axis gradient magnetic field Gz as well as RF pulse. Also, the sequence controller 41 receives the raw data of the MR signal from the RF receiver 40 and inputs the MR signal to the medical image processing apparatus 50.

The medical image processing apparatus 50 includes processing circuitry 51, memory circuitry 52, input circuitry 53, a display 54, and communication control circuitry 55. Configurations of the processing circuitry 51, memory circuitry 52, input circuitry 53, display 54, and communication control circuitry 55 are the same as those of the processing circuitry 11, memory circuitry 12, input circuitry 13, display 14, and communication control circuitry 15 shown in FIG. 1, and thus description thereof will be omitted.

The medical image processing apparatus 50 displays imaging sequence condition setting screen information on the display 54. The input circuitry 53 provides a user with a function to set imaging sequence conditions and image processing conditions.

The medical image processing apparatus 50 places the raw data of the MR signal received from the sequence controller 41, as k-space data, applies an image reconstruction process including two-dimensional Fourier transform, generates image data of each slice of the subject P, applies predetermined image processing, and stores the image data subjected to the image processing in the memory circuitry 52.

The memory circuitry 52 stores conditions of the imaging sequence, information about the subject P (patient information), and the like used to generate the image data, by attaching them to the image data as supplementary information.

The medical image processing apparatus 50 displays the imaging sequence condition setting screen and the image data generated by imaging on the display 54 as images.

Figure 10:
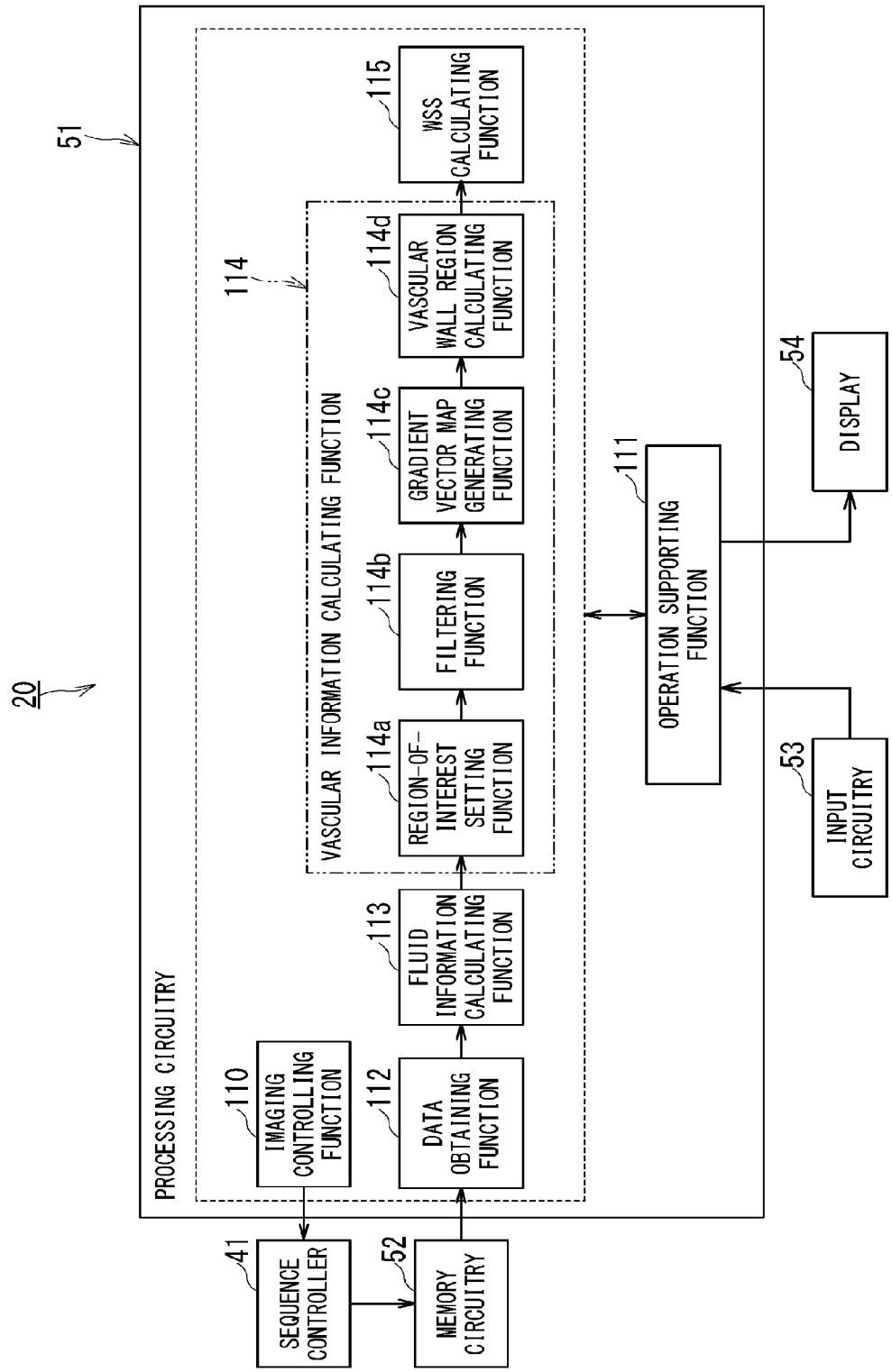
FIG. 10 is a block diagram showing functions of the MRI apparatus according to the second embodiment.

FIG. 10 is a block diagram showing functions of the MRI apparatus 20 according to the second embodiment.

As the processing circuitry 51 executes programs, the MRI apparatus 20 implements an imaging controlling function 110, an operation supporting function 111, a data obtaining function 112, a fluid information calculating function 113, a vascular information calculating function 114, and a WSS calculating function 115.

Note that although it is assumed in the example described below that the functions 110 to 114 of the MRI apparatus 20 operate in software fashion, some or all of the functions 110 to 114 may be provided in the MRI apparatus 20 in hardware fashion. In the MRI apparatus 20 shown in FIG. 10, the same functions as those in medical image processing apparatus 10 shown in FIG. 2 are denoted by the same reference numerals as the corresponding functions in FIG. 2, and description thereof will be omitted.

By controlling operation of the imaging apparatus 30 via the sequence controller 41, the imaging controlling function 110 images the subject by phase contrast magnetic resonance imaging, and collects four-dimensional MRI image data which can be used to calculate a four-dimensional velocity vector, as four-dimensional image data. The imaging controlling function 110 stores the four-dimensional MRI image data in the memory circuitry 52.

The MRI apparatus 20 according to the second embodiment can accurately and precisely calculate the vascular wall region used to calculate WSS, based on the four-dimensional MRI image data which can be used to calculate a four-dimensional velocity vector data made up of three spatial dimensions and multiple time phases.

(Variation)

A variation of the medical image processing apparatus 10 (or MRI apparatus 20) will be described with reference to FIG. 2 (or FIG. 10).

The vascular information calculating function 114 calculates the four-dimensional vascular wall region W (illustrated in FIG. 7) based on the four-dimensional blood flow velocity vector data in multiple time phases. By expanding and contracting (through coordinate transformation) another image in one time phase generated by a scan (such as TOF: time of flight) different from a scan for calculation of WSS such that a difference between a vascular wall region on the other image and the four-dimensional vascular wall region W will be equal to or smaller than a threshold, the vascular information calculating function 114 can generate other images in multiple time phases, i.e., another four-dimensional image.

The WSS calculating function 115 displays the images in multiple time phases making up the other four-dimensional image generated by the vascular information calculating function 114 on the display 14 (or display 54) by adding a value of calculated WSS to the images.

Figure 11:
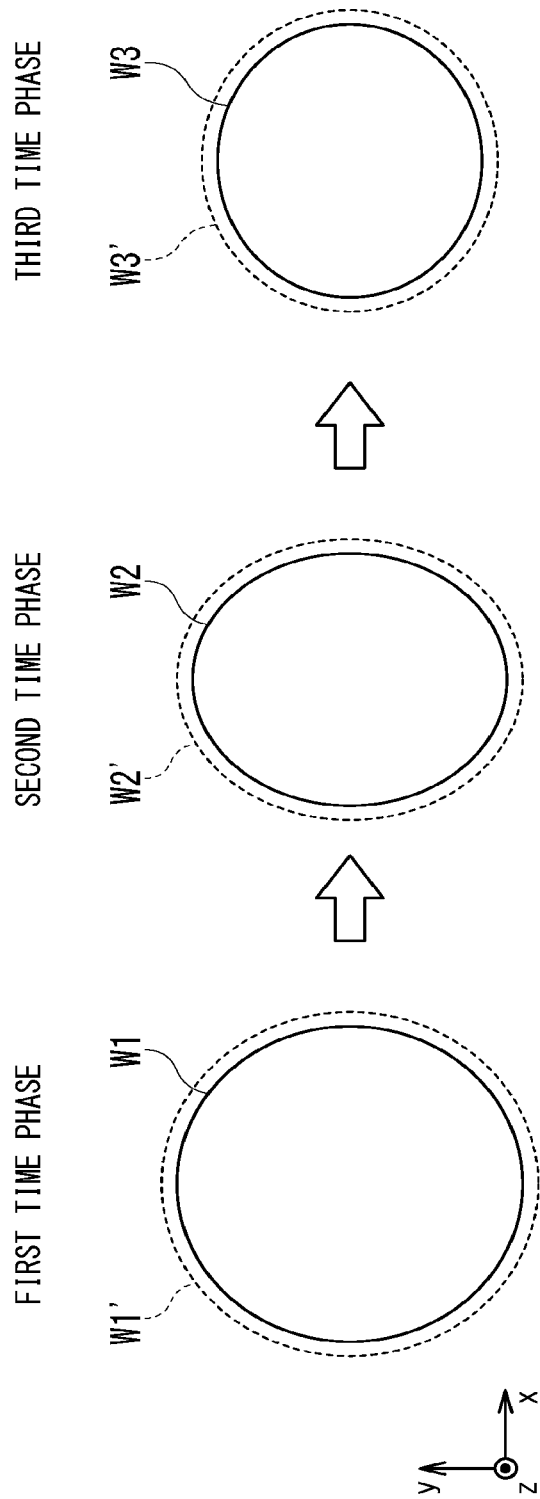
FIG. 11 is a diagram to illustrate a method for generating another four-dimensional image based on another image in one time phase.

FIG. 11 is a diagram to illustrate a method for generating another four-dimensional image based on another image in one time phase.

FIG. 11 shows the vascular wall region W shown in FIG. 7, i.e., the vascular wall region W in a first time phase (a vascular wall region W1), the vascular wall region W in a second time phase (a vascular wall region W2), and the vascular wall region W in a third time phase (a vascular wall region W3). Also, FIG. 11 shows vascular wall regions W1', W2', W3' which result when the other image in the one time phase is expanded and contracted based on the vascular wall regions W1, W2, and W3. Image display shown in FIG. 11 allows the vascular wall regions W1', W2', and W3' to be displayed with higher accuracy than the vascular wall region W obtained in the first and second embodiments.

A method for setting a region of interest and identifying a vascular wall region in the region of interest based on a velocity vector in the region of interest has been described in the embodiments. However, the vascular wall region may be identified based on the velocity vector in an entire region including the region of interest. When a region of interest has been established, a wall region is identified only in the region of interest, allowing the processing circuitry 11 (or processing circuitry 51) to calculate a wall region only in a desired region relatively quickly.

The method for identifying a branch vessel using a velocity vector of blood has been illustrated in the present embodiments by taking a blood vessel in which blood flows as an example of luminal bodies in which a fluid flows. However, luminal bodies are not limited to blood vessels. For example, the luminal bodies may be perineural spaces in which cerebrospinal fluid (CSF) flows or lymph vessels in which lymph fluid flows.

The medical image processing apparatus and the medical image processing method according to at least one of the present embodiments described above can improve calculation accuracy of WSS.

The term "processing circuitry" refers to, in addition to a dedicated or general-purpose CPU (central processing unit) or MPU (microprocessor unit), an application specific integrated circuitry (ASIC) and a programmable logic device or the like. A simple programmable logic device (SPLD), a complex programmable logic device (CPLD) and a field programmable gate array (FPGA) may be mentioned as examples of the programmable logic device. The processing circuitry reads out and executes a program that is stored in a memory or is directly incorporated into the processing circuitry.

The processing circuitry may be constituted by a single circuit, or may be constituted by combining independent multiple circuits. In the latter case, a memory may be individually provided for each circuit of the multiple circuits, or a program corresponding to the functions of the multiple circuits may be stored in a single memory.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image processing apparatus comprising; processing circuitry configured to:
    calculate fluid information including a velocity vector based on three-dimensional phase image data in multiple time phases, the three-dimensional phase image data being collected by phase contrast magnetic resonance imaging, and the three-dimensional phase image data representing a fluid flowing through a lumen,
    identify a wall region of the lumen based on a gradient vector on a section including the lumen, the gradient vector being calculated from a magnitude and a direction of the velocity vector, and
    calculate wall shear stress using the wall region and the fluid information.

2. The medical image processing apparatus according to claim 1,
    wherein the processing circuitry is configured to identify the wall region based on the gradient vector on a minor axis section of the lumen.

3. The medical image processing apparatus according to claim 1, wherein the processing circuitry is configured to:
    transform, based on the wall region three-dimensional image data collected by imaging, the three-dimensional image data different from the three-dimensional phase image data, and
    display a value of the calculated wall shear stress on the transformed three-dimensional image data in superposition.

4. The medical image processing apparatus according to claim 1, wherein the processing circuitry is configured to:
    calculate the fluid information including the velocity vector based on the three-dimensional phase image data in the multiple time phases, the three-dimensional phase image data representing a fluid flowing through a blood vessel as the lumen, and
    identify the wall region of the blood vessel based on the velocity vector.

5. The medical image processing apparatus according to claim 4, wherein the processing circuitry is configured to:
    set a region of interest based on the velocity vector, and
    identify the wall region based on the velocity vector in the region of interest.

6. The medical image processing apparatus according to claim 5,
    wherein the processing circuitry is configured to identify the wall region in each of slices based on the gradient vector on a minor axis section of the blood vessel, the gradient vector being calculated from the magnitude and the direction of the velocity vector on each of minor axis sections in the region of interest.

7. The medical image processing apparatus according to claim 5,
    wherein the processing circuitry is configured to establish a set of voxels whose velocity vector is equal to or larger in magnitude than a threshold as a region of interest by selecting the set of voxels from among voxels based on the velocity vector.

8. The medical image processing apparatus according to claim 7, wherein the processing circuitry is configured to:
set one region of interest based on data of the velocity vector in multiple time phases, and
set one region of interest at a same position of the velocity vector.

9. The medical image processing apparatus according to claim 1,
wherein the processing circuitry is configured to display the wall region on a display.

10. The medical image processing apparatus according to claim 1, wherein the processing circuitry is configured to:
calculate, based on the velocity vectors, velocity absolute values of fluid of respective voxels included in the section,
calculate gradient vectors of the respective voxels, the gradient vectors each including a direction with the largest change in magnitude of the velocity absolute value among directions on the section, and
identify, based on the gradient vectors, a wall region of the lumen.

11. The medical image processing apparatus according to claim 1, wherein the processing circuitry is configured to:
plot the magnitudes of the gradient vectors on the respective voxels included in the section, thereby generating a distribution, and
identify, based on the distribution, the wall region in the section.

12. A medical image processing apparatus comprising:
processing circuitry configured to:
calculate fluid information including a velocity vector based on three-dimensional image data in multiple time phases, the three-dimensional image data representing a fluid flowing through a lumen,
identify the wall region of the lumen based on a gradient vector on a minor axis section of the lumen, the gradient vector being calculated from a magnitude and a direction of the velocity vector, and
calculate wall shear stress using the wall region and the fluid information.

13. A medical image processing method comprising:
calculating fluid information including a velocity vector based on three-dimensional phase image data in multiple time phases, the three-dimensional phase image data being collected by phase contrast magnetic resonance imaging, and the three-dimensional phase image data representing a fluid flowing through a lumen;
identifying a wall region of the lumen based on a gradient vector on a section including the lumen, the gradient vector being calculated from a magnitude and a direction of the velocity vector, and
calculating wall shear stress using the wall region and the fluid information.

* * * * *